US012661292B2

(12) United States Patent　　　　(10) Patent No.:　US 12,661,292 B2
Kota et al.　　　　　　　　　　　　(45) Date of Patent:　　Jun. 23, 2026

(54) PERSONAL RESPIRATORY ISOLATION SYSTEM

(71) Applicants: THE REGENTS OF THE UNIVERSITY OF MICHIGAN, Ann Arbor, MI (US); INSPIRE RX, LLC, Ann Arbor, MI (US)

(72) Inventors: Shalini Sarala Kota, Ann Arbor, MI (US); Sridhar Kota, Ann Arbor, MI (US); Kevin R. Ward, Superior Township, MI (US); David Hornick, Ann Arbor, MI (US)

(73) Assignees: THE REGENTS OF THE UNIVERSITY OF MICHIGAN, Ann Arbor, MI (US); INSPIRE RX, LLC, Ann Arbor, MI (US)

( * ) Notice: Subject to any disclaimer, the term of this patent is extended or adjusted under 35 U.S.C. 154(b) by 937 days.

(21) Appl. No.: 17/910,317

(22) PCT Filed: Mar. 30, 2021

(86) PCT No.: PCT/US2021/024830
§ 371 (c)(1),
(2) Date: Sep. 8, 2022

(87) PCT Pub. No.: WO2021/202488
PCT Pub. Date: Oct. 17, 2021

(65) Prior Publication Data
US 2023/0032878 A1　　Feb. 2, 2023

Related U.S. Application Data

(60) Provisional application No. 63/010,208, filed on Apr. 15, 2020, provisional application No. 63/005,117,
(Continued)

(51) Int. Cl.
*A61G 10/02*　　(2006.01)
*A61M 16/00*　　(2006.01)
(Continued)

(52) U.S. Cl.
CPC ....... *A61G 10/023* (2013.01); *A61M 16/0003* (2014.02); *A61M 16/0666* (2013.01); *A61M 16/1055* (2013.01)

(58) Field of Classification Search
CPC .............. A61B 90/40; A61B 2090/401; A41D 13/002–0025; A41D 13/11–1192; A61M 16/06–0694; A62B 17/04
See application file for complete search history.

(56) References Cited

U.S. PATENT DOCUMENTS 3,680,557 A * 8/1972 Doniguian ............. A61G 10/04
　　　　　　　　　　　　　　　　　　　392/407
3,710,791 A * 1/1973 Deaton .................. A61G 11/00
　　　　　　　　　　　　　　　　　　　135/117
(Continued)

OTHER PUBLICATIONS

International Application No. PCT/US2021/024830, International Search Report and Written Opinion, mailed Aug. 30, 2021.
(Continued)

*Primary Examiner* — Thaddeus B Cox
(74) *Attorney, Agent, or Firm* — MARSHALL, GERSTEIN & BORUN LLP

(57) ABSTRACT

A personal respiratory isolation system (PRIS) provides a personal, negative pressure environment for a patient or user that reduces contamination and spread of pathogens exhaled by the patient into the environment. The PRIS includes an enclosure to receive the patient's head (such as a hood and a drape) and a negative pressure source which draws ambient air into the interior of the enclosure and draws air within the enclosure's interior (including the exhalations of the patient, including any contaminants and/or pathogens) out of
(Continued)

the enclosure via a fluid port into a container for biohazard processing or disposal. The PRIS may allow positive air pressure therapeutic treatments to be delivered to the patient within the negative pressure environment, and the PRIS may maintain a constant pressure within the interior of the enclosure. The PRIS may include a transparent, hinged face shield for ease of patient observation and/or access.

20 Claims, 6 Drawing Sheets

Related U.S. Application Data filed on Apr. 3, 2020, provisional application No. 63/002,120, filed on Mar. 30, 2020.

(51) Int. Cl.
    *A61M 16/06*        (2006.01)
    *A61M 16/10*        (2006.01)

(56)                References Cited

U.S. PATENT DOCUMENTS

| | | | | |
|---|---|---|---|---|
| 3,955,570 | A | * | 5/1976 | Hutter, III .............. A61B 90/40 |
| | | | | 128/863 |
| 4,832,042 | A | * | 5/1989 | Poppendiek ...... A61M 16/0627 |
| | | | | 128/205.26 |
| 4,949,714 | A | * | 8/1990 | Orr ................... A61M 16/0627 |
| | | | | 128/200.24 |
| 5,335,653 | A | * | 8/1994 | Blomqvist .......... A61M 16/085 |
| | | | | 128/200.24 |
| 2004/0255937 | A1 | * | 12/2004 | Sun ........................ A61G 10/00 |
| | | | | 128/201.25 |
| 2005/0085686 | A1 | * | 4/2005 | Yuen .................... A61G 10/005 |
| | | | | 312/1 |
| 2007/0113856 | A1 | | 5/2007 | Acker et al. |
| 2009/0018571 | A1 | * | 1/2009 | Whalen .................. A63B 22/02 |
| | | | | 606/201 |
| 2010/0108067 | A1 | | 5/2010 | Walker et al. |
| 2011/0240017 | A1 | * | 10/2011 | Butler ................... A61M 16/06 |
| | | | | 128/201.25 |
| 2012/0285468 | A1 | | 11/2012 | Birch |
| 2015/0313506 | A1 | * | 11/2015 | Borsari ................ G01N 33/004 |
| | | | | 600/532 |
| 2016/0030779 | A1 | | 2/2016 | Twu et al. |
| 2020/0179219 | A1 | * | 6/2020 | Petersen .............. A61H 9/0057 |

OTHER PUBLICATIONS

International Application No. PCT/US2021/024830, Written Opinion of the International Preliminary Examining Authority, mailed Feb. 25, 2022.

International Application No. PCT/US2021/024830, International Preliminary Report on Patentability, mailed Jun. 29, 2022.

* cited by examiner

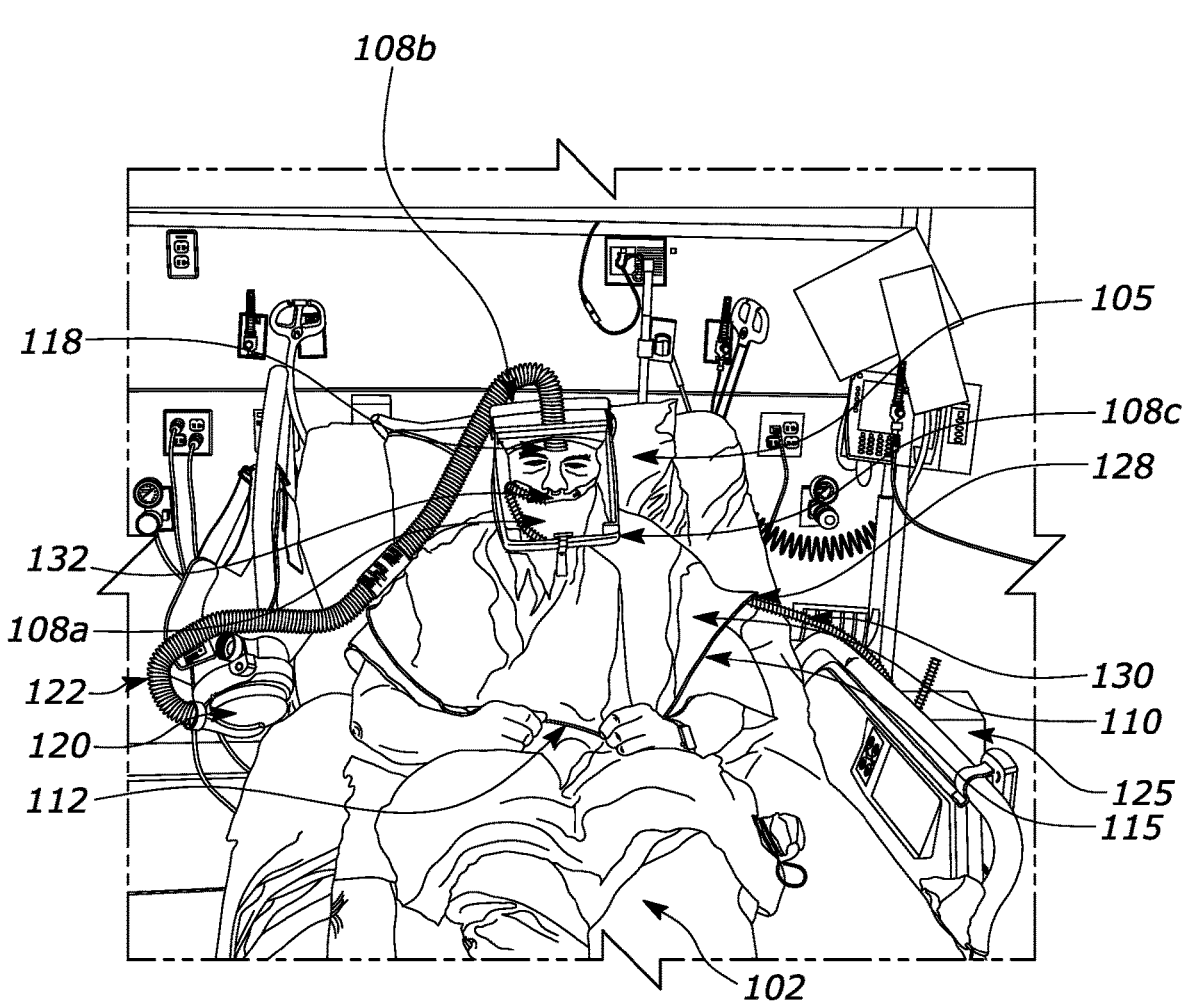
FIG. 1A

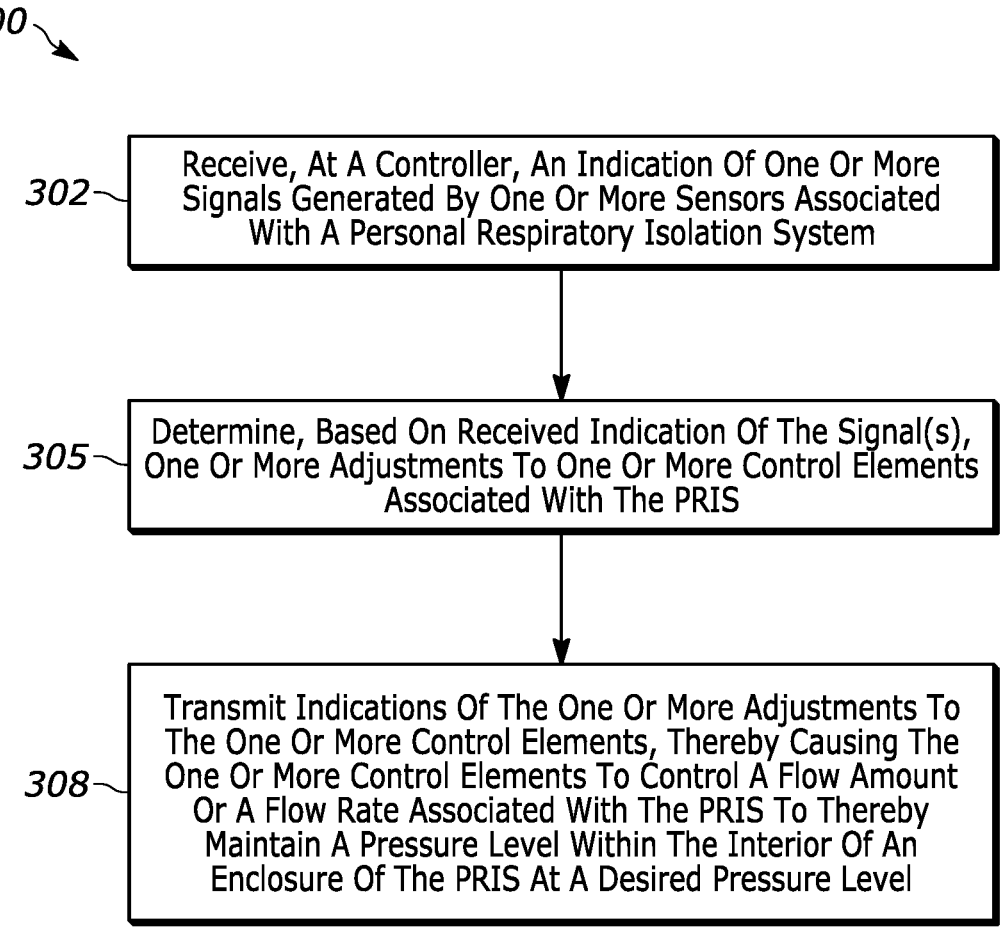

*300*

302 — Receive, At A Controller, An Indication Of One Or More Signals Generated By One Or More Sensors Associated With A Personal Respiratory Isolation System 305 — Determine, Based On Received Indication Of The Signal(s), One Or More Adjustments To One Or More Control Elements Associated With The PRIS 308 — Transmit Indications Of The One Or More Adjustments To The One Or More Control Elements, Thereby Causing The One Or More Control Elements To Control A Flow Amount Or A Flow Rate Associated With The PRIS To Thereby Maintain A Pressure Level Within The Interior Of An Enclosure Of The PRIS At A Desired Pressure Level

FIG. 3

PERSONAL RESPIRATORY ISOLATION SYSTEM

CROSS-REFERENCE TO RELATED APPLICATIONS

This application is a National Stage application of International Application No. PCT/US2021/024830, filed Mar. 30, 2021, which claims priority to and the benefit of U.S. Provisional Patent Application No. 63/010,208, filed on Apr. 15, 2020 and entitled "PERSONAL RESPIRATORY ISOLATION SYSTEM," and which claims priority to and the benefit of U.S. Provisional Patent Application No. 63/005, 117, filed on Apr. 3, 2020 and entitled "PERSONAL RESPIRATORY ISOLATION SYSTEM," and further which claims priority to and the benefit of U.S. Provisional Patent Application No. 63/002,120, filed on Mar. 30, 2020 and entitled "PERSONAL RESPIRATORY ISOLATION SYSTEM (PRIS)," the entire contents of which are incorporated by reference herein.

FIELD OF THE DISCLOSURE

The application relates generally to medical equipment, and in particular relates to medical equipment that aids in preventing a person who has or may potentially have a contagious respiratory condition from spreading the condition into his or her environment and, in some embodiments, simultaneously providing therapeutic treatment to the person.

BACKGROUND

The rapid spread of the infectious COVID-19 coronavirus disease has been deemed a worldwide pandemic. As is presently known, the COVID-19 virus causes respiratory illness with symptoms such as a fever, a cough, and in some cases, difficulty in breathing, and is spread primarily through contact with aerosol droplets expelled by an infected person when they cough, sneeze, or even merely breathe, and/or when a previously uninfected person touches a surface or object that has the virus on it (e.g., due to droplet-aerosol spread), and then touches their own eyes, nose, or mouth. Also as is presently known, in some cases, infected persons may not exhibit any physical symptoms associated with COVID-19 and feel entirely healthy, but may nonetheless may spread the virus to others.

COVID-19 and other highly transmissible respiratory illnesses have the potential to quickly overwhelm hospital capacity and available medical resources. For example, as COVID-19 can rapidly evolve to acute hypoxemia and respiratory distress syndrome-type illness, numerous mechanical ventilators may be needed to treat infected patients. Other medical resources which are needed to treat patients who have or who are suspected to have COVID-19 or other highly transmissible respiratory illnesses include negative air pressure rooms in which the patients may be sequestered to aid in mitigating droplet-aerosol spread to others in the hospital or medical facility, and personal protective equipment or PPE (such as gloves, face masks, gowns, drapes, goggles, shields, etc.) worn by health care providers to protect them from contracting the illness from the patients who are under their care. These and other critical medical resources may quickly become limited and in short supply (if at all) when the illness(es) spread rapidly throughout a population, e.g., during a pandemic.

For patients who have trouble breathing, but whose condition is not critical enough to warrant the use of a mechanical ventilator, health care providers may outfit them with a heated high flow nasal cannula (HFNC). HFNCs may be utilized for such types of patients, as well as for patients who suffer from hypoxic respiratory failure and other types of conditions resulting from respiratory illnesses such as COVID-19. HFNCs may deliver a heated, humid mixture of ambient air and oxygen (or, in some cases, pure oxygen) to patients at flows up to 60-100 liters per minute. Use of HFNCs may aid in liberating patients from mechanical ventilator use as their conditions improve, and may more generally free up supplies of mechanical ventilators for use by patients that are in more critical condition, as less critical patients may be serviced by HFNCs.

However, the use of HFNCs may present various risks and challenges when utilized by patients who have or who are suspected of having COVID-19 or other highly transmissible respiratory illnesses. For example, the high flow rate delivered by HFNCs may cause or increase the aerosolization of viruses and/or of bacteria residing in the patient, and in particular, when the patient coughs. The impact of such droplet-aerosol spread is further exacerbated by the limited supply of negative pressure rooms during pandemics, and is not easily mitigated by having patients wear face masks, as patients utilizing HFNCs typically do not tolerate mask coverings well. For example, use of an HFNC may cause masks to fog up and provide an uncomfortably humid environment for the patient. Further, many systems prohibit the use of nasal cannula flows above 6 liters per minute (e.g., at least due to potential aerosolization of viruses and/or bacteria from the respiratory system of the user at flow levels greater than 6 liters per minute), which results in patients being intubated earlier than would otherwise be needed, and in some cases, needlessly. Similar risks and challenges exist when patients are administered bronchodilator aerosols and other therapeutic treatments while utilizing HFNCs.

SUMMARY

Embodiments of the Personal Respiratory Isolation System (PRIS) disclosed herein provide a personal isolation system for individual use by a patient who has or who is suspected of having a transmissible respiratory illness, such as COVID-19. Generally speaking, the embodiments of the PRIS provide a personal, negative pressure environment for the user that reduces contamination and potential spread of viral and/or bacterial pathogens that are expelled and/or exhaled by the user into the environment in which the user is located. Further, some embodiments of the PRIS may also simultaneously provide the user with therapeutic and/or medicinal treatments, and/or may simultaneously provide protection for an immunocompromised user.

The PRIS includes an enclosure which is particularly designed and configured to contain a negative pressure environment into which the user breathes, and thereby isolating respiratory fluid (e.g., air and/or liquid) that is exhaled and/or expelled by the user (e.g., via the user's nose and/or mouth) and preventing the user's fluid outflow from being dispersed directly into the user's surroundings. The respiratory fluid outflow of the user may include bacterial and/or viral pathogens, aerosol particles produced from aerosolizing or potentially aerosolizing procedures and/or therapies to which the user has been subjected, and the like.

The enclosure of the PRIS may include a fluid output port coupled to a negative pressure source (e.g., a vacuum, a reverse fan and motor combination, etc.) that is disposed outside of the PRIS' enclosure. During operations, the negative pressure source may draw ambient air into the interior of the enclosure, e.g., via one or more openings in the enclosure that allow ambient air to enter. Such openings may be inherently provided by one or more components of the PRIS (such as via the aperture via which the user enters into the enclosure, via the folds of a flexible drape that is included in the PRIS, etc.), and/or such openings may be passively provided by the PRIS, e.g., via general cracks and/or gaps that are present between unsealed components of the PRIS. In some embodiments, the enclosure of the PRIS may additionally or alternatively include an explicit inflow port via which ambient air is allowed to enter into the enclosure. For example, an explicit, ambient air inflow port may be disposed in a rigid portion of the PRIS. As such, the intentionally unsealed or "leaky" nature of the PRIS allows the movement of ambient air into the enclosure's interior, which not only allows the user to breathe air that not circulated or re-circulated, but also may cool and/or dehumidify the interior of the enclosure (such as when the user is wearing a heated respiratory device) for the user's comfort and ease of use.

At any rate, in addition to drawing ambient air into the interior of the enclosure via one or more ambient air openings, the negative pressure source may also (e.g., simultaneously) draw air that is disposed within the interior of the enclosure (which includes both drawn ambient air and the user's fluid outflow) through the fluid output port. As such, the PRIS allows the user's fluid outflow to be collected in a controlled manner. The collected fluid outflow may be filtered to collect pathogenic particles and/or may be treated with a pathogen-impairing technique (such as ultra-violet radiation, high temperatures, autoclaving, etc.) prior to venting the outflow into the environment. In some embodiments, the interior air that is drawn through the fluid output port may be collected into a container for safe, biohazard processing or disposal.

In some embodiments, the PRIS may additionally deliver ambient air, oxygen, aerosolized medicine, and/or other therapeutic treatments to the user as the user is disposed within the personal, negative pressure environment provided by the PRIS. Generally, these therapeutic treatments may be directly administered to the user within the negative pressure environment via a direct, positive air pressure mechanism or technique, such as via a heated, high flow nasal cannula, a continuous positive airway pressure (CPAP) device, an oxygen face mask that delivers oxygen and/or aerosol treatments, and the like. In some use cases, though, the user may wear, in conjunction with the PRIS, some other type of respiratory device that does not provide positive airway pressure, such as a passive face mask.

In some embodiments, the PRIS may maintain the negative pressure level within the interior of the enclosure at a desired pressure level. For example, the amount and/or the flow rate at which interior air is drawn through the fluid output port may be detected and controlled to maintain the desired pressure level. Additionally or alternatively, in embodiments in which direct therapeutic treatments are administered to the user within the negative pressure environment, the amount and/or the flow rate at which such treatments are administered may be detected and controlled to maintain the desired pressure level within the enclosure's interior. Still additionally or alternatively, in embodiments, the amount and/or the flow rate at which ambient air is drawn into the interior of the enclosure may be detected and controlled to maintain the desired pressure level within the enclosure's interior.

In accordance with a first example embodiment, a personal respiratory isolation system (PRIS) includes an enclosure that includes an aperture configured to receive only a portion of a body of a user into an interior of the enclosure so that a nose and a mouth of the user are contained within the enclosure. Additionally, the enclosure includes one or more rigid portions, at least a part of which is disposed to shield the nose and the mouth of the user from an environment in which the user is located while the nose and the mouth of the user are contained within the enclosure, the at least the part of the one or more rigid portions which is disposed to shield the nose and the mouth of the user being a shield. The shield may be substantially rigid or flexible, for example. The enclosure further includes an opening via which ambient air enters into the interior of the enclosure, and a flow output port that is coupled to a negative pressure source disposed outside of or external to the enclosure. The negative pressure source is operable to draw air that is disposed within the interior of the enclosure through the flow output port to thereby provide or produce a negative pressure within the interior of the enclosure, where the drawn interior air including fluid that has been at least one of exhaled or expelled by the user.

In accordance with a second example embodiment, a method of controlling a pressure of a personal respiratory isolation system (PRIS) that is being utilized by a user is disclosed. The PRIS whose pressure is controlled by the method includes an enclosure, and the enclosure includes an aperture via which only a portion of a body of the user has been received into an interior of the enclosure so that a nose and a mouth of the user are contained within the enclosure. Additionally, the enclosure includes a particular portion shielding the nose and the mouth of the user from an environment in which the user is located, and an opening via which ambient air is allowed to enter into the interior of the enclosure. The enclosure further includes a flow output port through which air that is disposed within the interior of the enclosure is being drawn by a negative pressure source. The negative pressure source is coupled to the flow output port and is disposed outside of (e.g., external to) the enclosure, and the interior air that is being drawn through the fluid output port includes (i) fluid that has been at least one of exhaled or expelled by the user, and (ii) ambient air that has been drawn, by the negative pressure source, into the interior of the enclosure via the opening.

The method includes, at a controller communicatively connected to one or more control elements associated with the PRIS, receiving, at the controller via one or more communication interfaces, an indication of a signal generated by a sensor, where the signal is indicative of at least one of: an amount or a flow rate of the air that is being drawn by the negative pressure source from the interior of the enclosure through the flow output port. The method also includes determining, by the controller and based on the indication of the signal, one or more adjustments to the one or more control elements; and transmitting, by the controller via the one or more communication interfaces, respective indications of the one or more adjustments to the one or more control elements, thereby causing the one or more control elements to control, in accordance with the one or more adjustments, the at least one of the amount or the flow rate of the interior air that is being drawn through the flow output port, thereby maintaining a desired level of negative pressure within the interior of the enclosure.

BRIEF DESCRIPTION OF THE DRAWINGS

FIG. 1A illustrates an embodiment of Personal Respiratory Isolation System (PRIS) being utilized by an individual.

FIG. 3 is a flow diagram of an example method corresponding to controlling embodiments of the PRIS.

DETAILED DESCRIPTION

Figure 1B:
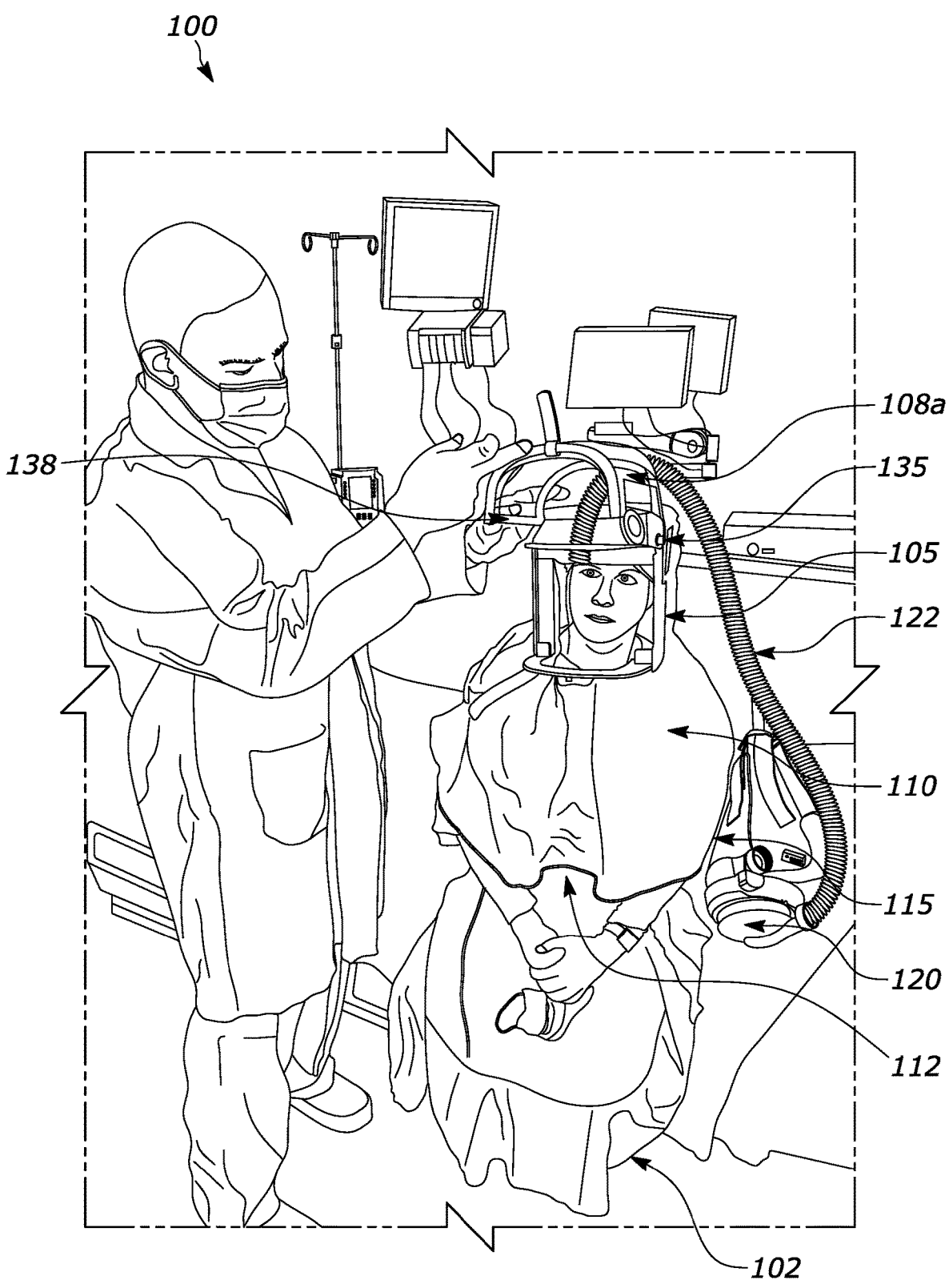
FIG. 1B illustrates the Personal Respiratory Isolation System (PRIS) of FIG. 1A with the shield in an open position.

Although the following text discloses a detailed description of example methods, apparatus and/or articles of manufacture, it should be understood that the legal scope of the property right is defined by the words of the claims set forth at the end of this patent. Accordingly, the following detailed description is to be construed as examples only and does not describe every possible example, as describing every possible example would be impractical, if not impossible. Numerous alternative examples could be implemented, using either current technology or technology developed after the filing date of this patent. It is envisioned that such alternative examples would still fall within the scope of the claims.

FIG. 1A illustrates an example embodiment 100 of a Personal Respiratory Isolation System that is being utilized by an individual or user 102. As shown in FIG. 1A, the PRIS 100 includes an enclosure 105 having one or more rigid portions 108a, 108b, 108c and one or more flexible portions 110. The enclosure 105 of the PRIS 100 includes an aperture 112 via which only a portion of (and not the entirety of) the user's body 102 is received into an interior of the enclosure 105. For example, the aperture 112 may receive the user's nose and mouth, the user's face, the user's head, the user's head and part of the user's neck, etc. into the interior of the enclosure 105. In the embodiment 100 shown in FIG. 1A, the face, neck, and the head of the user 102 have been received into the interior of the enclosure 105 via its aperture 112, where the aperture 112 is formed by both the rigid portions 108 and the flexible portions 110 of the enclosure 105.

The one or more rigid portions 108 of the enclosure 105 include a physical barrier 108b that shields the user's nose and mouth (and in some implementations, such as illustrated in FIG. 1A, at least a majority of the user's face) from his or her surroundings and/or vice versa. The shield 108a may be rigid, substantially rigid, or flexible, for example. The term "substantially rigid," as utilized here, generally refers to materials that have the character of being able to self-maintain a stiff, three-dimensional shape in the absence of any external force being applied, but which may bend to some degree without breaking when a sufficient external force is applied. That is, a "substantially rigid" material may be rigid enough to provide its own structural support without being brittle. For example, glass may be a rigid material, whereas some types of plastic (such as plastics that are utilized as water and soda bottles) may be substantially rigid materials. On the other hand, the term "flexible," as utilized herein, refers to materials that are pliable and capable of easily bending without breaking when lesser amounts of external forces are applied, and typically rely on an external support to maintain a three-dimensional structure. For example, cloth, plastic bags, drapes, and capes may be flexible materials.

In FIG. 1A, the shield 108a is shown as being transparent, which conveniently allows health care workers to see and monitor the face of the user while the user is utilizing the PRIS 100. In some embodiments, though, the shield 108b may be semi-transparent, opaque, or solid. The enclosure 105 may include other rigid and/or substantially rigid portions 108b, 108c to which the shield 108a is coupled. As shown in FIG. 1A, the shield 108a is coupled to a frame 108b which in turn is coupled to a and/or to a helmet, hood, cap, or other hard-shell material 108c that covers at least a portion of the user's head. The rigid and/or substantially rigid portions 108a-108c of the enclosure 105 may have a structure or form factor and/or otherwise may be made of materials that have sufficient structural integrity to support or withstand the negative pressure within the interior of the enclosure, as well as to avoid (and/or not come into) direct contact with the user's nose and mouth. In some embodiments, the rigid and/or substantially rigid portions 108a-108c of the enclosure 105 may have a structure or form factor and/or otherwise may be made of materials that have sufficient structural integrity so as to avoid (and/or not come into) contact with a respiratory device and/or other therapeutic device(s) that are worn by the user and that are at least partially disposed within the interior of the enclosure 105. In some embodiments, the inherent structure of the PRIS 100 may allow a user to wear earbuds with or without microphones, headsets, and/or other portable communication devices to augment his or her hearing and/or to better or more easily communicate with health care workers. Additionally or alternatively, communication devices such as speakers and/or microphones may be integrated into the PRIS 100 to aid the user in communicating with health care workers.

In FIG. 1A, the enclosure 105 of the PRIS 100 includes one or more flexible portions 110, such as a drape, a cape, or other section of suitable pliable or supple material. The one or more flexible portions 110 may cover a part of the user's head and/or neck. In some embodiments, the one of more flexible portions 110 may cover the user's shoulders. The one or more flexible portions 110 may be attached (e.g., removably attached) to the one or more rigid portions 108, in an implementation. In some implementations, the one or more flexible portions 110 may not be attached at all to the one or more rigid portions 108. For example, the one or more flexible portions 110 may form a flexible hood that is first donned by the user 102, and the one or more rigid portions 108 may form a larger, more rigid hood that is subsequently placed over the flexible hood worn by the user 102.

In the embodiment 100, at least due to the one or more flexible portions 110, the enclosure 105 may not be entirely sealed to the surrounding environment while the user 102 is utilizing the PRIS 100. Ambient air may be allowed to enter the interior of the enclosure 105 via one or more opening(s) 115 which, in FIG. 1, are provided by the drape 110 and/or via the aperture 112. Said another way, in the embodiment 100, the ambient air openings 115 are included in the aperture 112, although in other embodiments, the ambient air openings 115 may be included or disposed in some other portion of the enclosure 105, such as one of the rigid portions 108.

As shown in FIG. 1A, the enclosure 105 of the PRIS 100 includes a flow output port 118 (not directly visible in FIG. 1A) to which a negative pressure source 120 (such as vacuum, or some other suitable reverse flow fan/motor combination) is coupled, e.g., via a hose or a tube 122. In some implementations, the negative pressure source 120 may be fluidly and removably coupled to the flow output port. The negative pressure source 120 is disposed outside of the enclosure 105 of the PRIS 100, and is operable to draw ambient air into the interior of the enclosure 105 (e.g., via one or more ambient air openings 115 of the enclosure 105), as well as to draw air that is disposed within the interior of the enclosure 105 through the flow output port 118 for eventual venting into the environment surrounding the user 102 and the PRIS 100. The interior air that is drawn by the negative pressure source 120 through the flow output port 118 may include a combination of drawn ambient air and fluid that has been exhaled and/or expelled by the user 102. As such, the drawing of the air disposed within the interior of the enclosure 105 by the negative pressure source 120 via the flow output port 118 creates a personal, negative pressure environment that surrounds the portion of the user 102 that has been received into the interior of the enclosure 105.

In some embodiments, in concert with creating the negative pressure environment surrounding the user in the interior of the enclosure 105, a fluid such as oxygen, therapeutics, and/or medicine may be delivered from an external fluid source 125 (not directly visible in FIG. 1A) to the user via a flow inlet 128 of the enclosure 105 and tubing 130. In the embodiment 100 shown in FIG. 1A, the flow inlet 128 is provided by the drape 110 and/or via the aperture 112. Said another way, in the embodiment 100, the flow inlet 128 is included in the aperture 112, although in other embodiments, the flow inlet 128 may be included in, disposed in, and/or provided by some other portion of the enclosure 105, such as one of the rigid portions 108. The flow inlet 128 of the enclosure 105 is configured to receive the tubing 130 into the interior of the enclosure 105, where the tubing 130 enables one or more desired fluids (e.g., one or more gases and/or liquids) to be delivered from the external fluid source 125 into the interior of the enclosure 105 for inhalation and/or ingestion by the user. For example, the tubing 130 may deliver oxygen, a therapeutic, and/or a medication to a nasal or other type of cannula, such as the heated high flow nasal cannula 132 shown in FIG. 1A. Alternatively, the tubing 130 may deliver the fluid from the external fluid source 125 directly to the user 102 via some other direct, positive airway pressure (PAP) device such as a facemask, a CPAP device, a multi-level PAP device, or other respiratory device which is disposed within the interior of the enclosure 105 and utilized by the user 102.

In some embodiments, the amount and/or the flow rate of interior air that is drawn by the negative pressure source 120 through the flow output port 118 may be adjusted and/or controlled (e.g., via one or more corresponding control valves coupled to the flow output port 118, the hose or tube 122, and/or the negative pressure source 120) to maintain a desired pressure within the enclosure 105. Typically, the desired pressure level within the enclosure 105 is some level of negative pressure; however, in some implementations, the desired pressure level within the enclosure 105 may be zero pressure. In embodiments in which the enclosure 105 also includes the flow inlet 128 via which the tubing 130 is received into the interior of the enclosure 105 to deliver desired fluid to the user 102, the amount and/or flow rate of fluid that is delivered directly to the user 102 via the tubing 130 may be independently adjusted and/or controlled (e.g., via one or more corresponding control valves coupled to the device 132, the tubing 130, and/or the external fluid source 125) to maintain the desired pressure within the enclosure

105. In some embodiments of the PRIS, the amount and/or flow rate of fluid that is delivered directly to the user 102 via the tubing 130 is adjusted and/or controlled in conjunction with the adjustment and/or control of the amount and/or flow rate of the interior air that is drawn through the flow output port 118 to thereby maintain the desired pressure within the enclosure 105.

During use of the PRIS 100, the air disposed within the interior of the enclosure 105 (which includes both drawn ambient air and fluid outflow that is exhaled and/or expelled by the user 102) may be drawn by the external pressure source through the flow output port 118 of the enclosure 118 for eventual venting into the environment surrounding the user 102 and the PRIS 100. As such, to protect the user's surroundings from contamination and spread of pathogens and/or therapeutic particles, the flow output port 118, the hose or tube 122, and/or the external pressure source 120 may include one or more filters (e.g., a HEPA filter, a medical grade filter, an active carbon filter, and/or other suitable types of filters, not visible in FIG. 1A) via which contaminants and/or particles included in the drawn interior air are filtered out prior to the remainder of the drawn interior air being vented into the surrounding environment. Additionally or alternatively, in some embodiments, the drawn interior air is subjected to a process and/or device that eliminates and/or impairs any viruses and/or bacteria disposed therein (for example, ultra-violet radiation, high temperature chamber, and/or other suitable process and/or device) prior to the drawn interior air being vented into the environment. The flow rate of interior air drawn by the external pressure source 120 may be controlled via valves, by varying the speed of a fan of the external pressure source 120, or in any other suitable manner.

FIG. 1B illustrates the Personal Respiratory Isolation System (PRIS) 100 of FIG. 1A with the shield 108a in an open position. As shown in FIG. 1B, the shield 108a is partially removed from a remainder of the enclosure 105, e.g., via a hinging mechanism 135. The ability of the shield 108a to be partially and/or entirely removed from the remainder of the enclosure 105 provides multiple benefits. For example, the user 102 may be provided food, drinks, and medicine in a solid form without having to take off or disassemble the PRIS 100. Additionally, additional and/or stronger suction may be applied while the shield 108a is in an open position to thereby further reduce the risk of contamination. While the attachment mechanism in the embodiment 100 is a hinging mechanism, other suitable attachment mechanisms may be alternatively or additionally utilized, such as hook-and-loop enclosures or other types of suitable attachment mechanisms. The ability of the shield 108a to be entirely removed also provides the benefit of being able to replace a shield 108a without needing to replace the remainder of the system 100 while the system 100 is being worn by the user 102.

As additionally shown in FIG. 1B, the PRIS 100 includes a seal 138 that seals openings between the shield 108a and the supporting frame 108b when the shield 108a is in a closed position. The seal 138 is optional, however, use of the seal 138 may help to more accurately maintain the desired negative pressure level within the interior of the enclosure 105.

In some embodiments, the interior face of the shield 108a may be coated with one or more anti-fogging coatings to help minimize an amount of fogging within the interior of the enclosure 105, e.g., when using an HFNC 132 or other heated device in conjunction with the PRIS 100. Additionally or alternatively, the shield 108a itself may be comprised of or manufactured from anti-fogging materials, e.g., anti-fogging glass, plastic, or the like. Nonetheless, in prototypes of the PRIS 100 in which the shield 108a was not treated with any anti-fogging coating and was not manufactured from anti-fogging materials, tests demonstrated that the negative pressure environment created by the negative pressure source 120 was sufficient to clear any fogging generated by the HFNC 132 within the interior of the enclosure 105, both when the shield 108a was in an open position as well as when the shield 108a was in a closed position, and even when the HFNC 132 was delivering heated fluids up to a rate of 60-100 liters per minute. Further, during the testing of the prototypes, no fog leaked out of the interior of the enclosure 105 into the surrounding environment, even when the shield 108a was in an open position.

Figure 2:
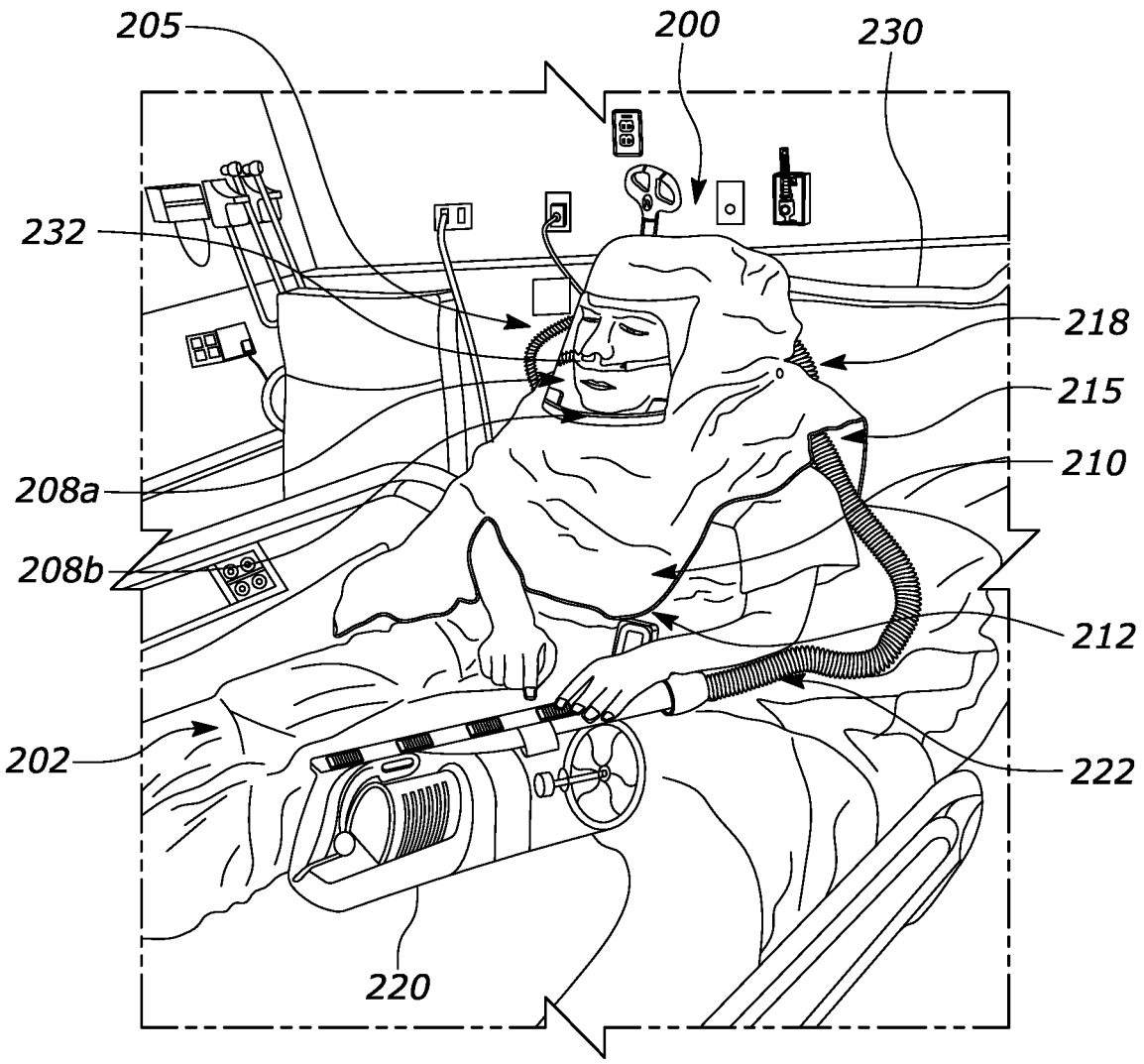
FIG. 2 illustrates another embodiment of a PRIS being utilized by an individual.

FIG. 2 illustrates another example embodiment 200 of a Personal Respiratory Isolation System that is being utilized by an individual or user 202. Similar to the PRIS 100 of FIG. 1A, the PRIS 200 includes an enclosure 205 having one or more rigid portions, e.g., a shield 208a and a frame 208b, and one or more flexible portions 210. However, in the PRIS 200, the helmet or hood rigid portion (e.g., the helmet 108c of FIG. 1) is omitted. As such, the shield 208a and frame 208b are directly coupled to the flexible portions 210, and the flexible portions 210 cover a part of the user's face, head, and neck. In some embodiments, the flexible portions 210 may at least partially cover the user's shoulders. Further similar to the PRIS 100, the enclosure 205 of the PRIS 200 includes an aperture 212, ambient air openings 215, and a flow output port 218 coupled, via a hose or tube 222, to an external negative pressure source 220. Still further similar to the PRIS 100, the enclosure 205 of the PRIS 200 includes a flow inlet (not visible in FIG. 2) via which tubing 230 delivers fluid from an external fluid source (also not visible in FIG. 2) into the interior of the enclosure 205 for at least one of inhalation or ingestion by the user 202. As shown in FIG. 2, the user 202 is wearing an HFNC 232 via which the external fluid is directly delivered into the user's airways. Optionally in the PRIS 200, respective control valves (not shown in FIG. 2) may be coupled to the personal, positive airway pressure or respiratory device 232, the tubing 230, the external fluid source, the external negative pressure source 220, the hose or tube 222, and/or the flow output port 218 to thereby control the level of pressure within the interior of the enclosure 205, which may be some level of negative pressure, or may be zero pressure. Additionally or alternatively, the flow of air drawn from the interior of the PRIS 200 through the flow output port 218 may be controlled by varying the fan speed of the negative pressure source 220, and/or by one or more other suitable mechanisms.

Of course, other embodiments of a Personal Respiratory Isolation System are possible. Generally, each embodiment may typically include an enclosure having an aperture via which only a portion of a user's body is received so that the user's nose and mouth are contained within the interior of the enclosure. The enclosure need not encircle the user's head, such as in the embodiments 100 and 200, so long as the enclosure includes a shield portion disposed to shield the user's nose and mouth from the user's surrounding environment. Further, the enclosure may be configured (e.g., in structure and in shape) to have sufficient integrity to maintain a negative pressure environment within its enclosure. Additionally, the enclosure may have a flow output port via which air disposed within the interior of the enclosure is drawn by a negative pressure source for eventual collection or venting into the user's surroundings. As such, embodiments of the PRIS in which the drawn interior air is eventually vented into the environment may include a filter and/or the drawn interior air may be subjected to a pathogen-impairing process prior to a remainder of the drawn interior air into user's surroundings, e.g., in manners such as previously described.

Embodiments of the PRIS need not include rigid or substantially portions. That is, in some embodiments, a majority of the enclosure may comprise flexible materials and/or portions, with the only possible rigid component being one that causes the aperture to remain sufficiently open to receive the user's head or other body part(s) into the enclosure's interior. In an embodiment, a PRIS may be implemented using a tent-like structure that comprises one or more substantially-rigid portions and/or flexible portions which are supported by a frame that may cover (only) a portion of the patient, e.g., while the patient is in a prone position. For example, the patient's torso and head may be disposed within the interior of the PRIS. At least some portions of the tent-like structure may be transparent. Advantageously, the structure or form factor of the tent allows the patient to wear other types of health care devices (e.g., monitors, intravenous and/or other types of catheters, etc.) while being in an isolated respiratory environment. In such embodiments, the PRIS may include one or more flaps which may be opened to allow health care workers to provide direct aid or treatments to the patient. While the flaps are in the open position, the draw of the negative pressure source may be increased to mitigate the spread of any pathogens while the flaps are in the open position, and may return back to the steady-state draw level after the flaps have been closed.

Indeed, in some embodiments of the tent-like PRIS, the tent structure may include different chambers, each of which is serviced by a different fluid outflow port. The different chambers may be drawn to the same level of pressure, or to different levels of pressure, if desired. For example, a respiratory chamber may enclose the user's head while a separate chamber may enclose the user's torso. As such, health care workers who are performing medical procedures on the torso of the user may be further protected from pathogen aerosolization generated by the user.

In other embodiments, the PRIS need not include flexible portions. For example, the enclosure of the PRIS may consist of only rigid portions, in embodiments.

In some embodiments, the PRIS may be a sealed environment. For example, after the head or other body part of the user has been received into the interior of the enclosure, the aperture may be sealed around the user. In these embodiments, ambient air may be allowed to enter into the enclosure's interior via an ambient air port that is disposed within a particular rigid portion or a particular flexible portion of the enclosure. The ambient air port may also be sealed from the environment, and an amount or a flow rate of ambient air drawn through the ambient air port (e.g., via the negative pressure source) may be adjusted and/or controlled (e.g., either individually, and/or in conjunction with other control valves) to maintain the pressure inside the enclosure at a desired level.

In some embodiments, the entire PRIS may be disposable, e.g., may be single use. In other embodiments, at least a portion of the rigid portion(s) of the PRIS's enclosure may be disposable or single use, and/or at least a portion of the flexible portion(s) of the PRIS's enclosure may be disposable or single use. In some embodiments, the entire PRIS may be made of materials which are able to be sterilized using any known medical-grade sterilization process (e.g., high temperatures, ultra-violet rays, cleaning agents, etc.) and re-used. In other embodiments, at least a portion of the rigid portion(s) of the PRIS' enclosure may be sterilizable and re-used, and/or at least a portion of the flexible portion(s) of the PRIS's enclosure may be sterilizable and re-used.

Other aspects and/or features which may be included in various embodiments of the PRIS may include one or more of the following:

1. The PRIS may include the negative pressure source.

2. The PRIS may include one or more adjustable fitting mechanisms to fit the PRIS to the user. The adjustable fitting mechanism(s) may be attached to the one or more rigid portions of the PRIS's enclosure (such as a plastic chin strap), and/or may be attached to the one or more flexible portions of the PRIS's enclosure (such as an adjustable cloth band or strap).

3. The PRIS may include one or more sensors that are positioned to sense the amount and/or the flow rate of ambient air being drawn into the interior of the enclosure, the amount and/or the flow rate of interior air being drawn through the flow output port of the enclosure, and/or the amount and/or flow rate of fluid being delivered into the interior of the enclosure for delivery to the user. Any of these sensors may operate in concert with one or more control elements that are individually and/or jointly operable to control the level of pressure within the interior of the enclosure.

4. The PRIS may include one or more sensors that are positioned to sense the temperature and/or the humidity within the interior of the enclosure and/or the ambient temperature. Any of these sensors may operate in concert with one or more control elements that are individually and/or jointly operable to control the temperature within the interior of the enclosure.

5. The PRIS may include one or more status indicators which may indicate a normal state and/or may indicate an alarm or an alert condition associated with the PRIS, e.g., an abnormal flow and/or pressure condition, an abnormal temperature, an abnormal level of humidity, etc. The status indicators may be visual and/or auditory, for example, and may operate in conjunction with outputs generated by one or more sensors, such as those described above and/or other types of sensors associated with the PRIS. For example, various status indicators may be associated with the level of pressure within the interior of the enclosure, the temperature within the interior of the enclosure, the amount of humidity within the interior of the enclosure, the proportion of ambient air and/or oxygen with respect to other gases disposed within the interior of the enclosure, the amount and/or the flow rate of ambient air being drawn into the interior of the enclosure, the amount and/or the flow rate of interior air being drawn through the flow output port of the enclosure, and/or the amount and/or flow rate of fluid being delivered into the interior of the enclosure for delivery to the user.

6. The flow outlet port of the PRIS may be integrally formed the one or more rigid portions of the enclosure.

7. The flow outlet port may have a means to removably couple with the hose or tube interconnecting the flow outlet port with the external source of negative pressure. The hose or tube may be an inlet hose of the external source of negative pressure, for instance.

8. The tubing that delivers fluid from the external fluid source may be inserted under one or more flexible portions of the enclosure to thereby enter into the interior of the enclosure.

9. The flow inlet may be a flow inlet port that is included in the one or more rigid portions of the enclosure or the one or more flexible portions of the enclosure.

10. The one or more flexible portions typically may cover the user's neck, and optionally, may cover at least a portion (e.g., the back) of the user's head. In an desirable but optional implementation, the one or more flexible portions may extend to cover (drape over) the shoulders of the user and/or other surfaces to thereby shield the user and/or other surfaces from any exhaled and/or expelled fluid that is not suspended within the air disposed within the interior of the enclosure or otherwise is not drawn through the outlet flow port of the PRIS.

11. The mass or volume flow of the external negative pressure source (e.g., vacuum) may be adjustable.

12. The inflow of fluid provided by the external fluid source and the outflow drawn by the external negative pressure source may be controlled and balanced to maintain a desired pressure inside the interior of the enclosure.

13. The outflow drawn by the external negative pressure source may be adjusted to control the amount of ambient air circulating through the interior of the enclosure.

14. Any of the surfaces of the PRIS (e.g., the interior faces and/or exterior faces of the one or more rigid portions, the interior faces and/or exterior faces of the one or more flexible portions, any ports and/or openings, etc.) may be coated with antiviral and/or antibacterial agents.

15. The enclosure may be equipped with embedded or integrated communication technology, e.g., speakers, microphones, etc. so that the wearer is able to easily communicate with health care workers, and in particular when respiratory devices that generate noise (such as HFNCs) are being utilized by the wearer. Alternatively, the enclosure may be sized to accommodate the user wearing/utilizing portable communication technologies while utilizing the PRIS, such as earbuds with microphones, headsets, and the like.

16. The negative pressure source (and indeed, any powered component of the PRIS) may be powered using any suitable power source, e.g., direct, wired connection with an outlet; direct, wireless connection with a wireless power source; battery; etc. In some embodiments, the negative pressure source may be supported by multiple power sources, which may be selectable, and/or of which at least one of may be a back-up power source. The power source may be able to be monitored and/or controlled, e.g., remotely and/or directly.

17. A portion of the enclosure of the PRIS that covers the lower jaw, chin, and/or neck area of the user may be removably attached, e.g., via a zipper, hook-and-loop materials, and/or another type of suitable attachment mechanism. In these embodiments, the removable portion may be quickly removed from the remainder of the PRIS, e.g., in an emergency situation, to provide medical personnel with quick and direct access to the user's lower jaw, chin, and/or neck area without having to remove the entire PRIS. The removable portion may be a separate component from the shield, in some embodiments. In other embodiments, the shield may extend to cover the user's lower jaw and chin (and optionally, the user's neck), and the extended shield may be able to be tilted open (e.g., via a hinging mechanism) or entirely removed from the remainder of the PRIS.

18. The system may be easily converted into a personal positive pressure environment. For example, a separate neck seal could be added, and the reverse flow fan may be removed. The enclosure may be insulated with oxygen, and a valve may be added to the flow output port to control the pressure within the interior of the enclosure to be a positive pressure. As such, the converted system may be used for the treatment of hypoxia and other conditions requiring positive pressure environments.

Of course, other aspects may be additionally or alternatively included in embodiments of the Personal Respiratory Isolation System described herein.

Turning now to FIG. 3, FIG. 3 depicts a flow diagram of an example method 300 of controlling a pressure of a Personal Respiratory Isolation System (PRIS) that is being utilized by a user. The method 300 may be performed in conjunction with embodiments of the Personal Respiratory Isolation System (PRIS) such as, for example, the PRIS 100, the PRIS 200, or other embodiments. The method 300 may include additional or alternate steps other than those described herein, if desired.

The method 300 may be performed by a controller that is communicatively connected to one or more control elements associated with the PR IS. The controller may be an industrial process controller or other suitable computing device having one or more communication interfaces that communicatively connect the controller to other devices, such as sensors, computing devices, and the like. The PRIS may include an enclosure, and the enclosure may include an aperture via which only a portion of a body of the user has been received into an interior of the enclosure so that a nose and a mouth of the user are contained within the enclosure. The enclosure may also include a substantially rigid or flexible portion shielding the nose and the mouth of the user from an environment in which the user is located, an opening via which ambient air enters into the interior of the enclosure, and a flow output port through which air that is disposed within the interior of the enclosure is being drawn by a negative pressure source. Typically, the negative pressure source is coupled to the flow output port and disposed outside of the enclosure, and the interior air includes (i) fluid that has been at least one of exhaled or expelled by the user, and (ii) ambient air that has been drawn, by the negative pressure source, into the interior of the enclosure via the opening.

At a block 302, the method 300 includes receiving, at the controller via one or more communication interfaces, an indication of a signal generated by a sensor that is associated with the PRIS. That is, the sensor may detect or sense some condition associated with operation of the PRIS. For example, the received indication of the sensor signal may be indicative of an amount or a flow rate of the interior air that is being drawn by the negative pressure source through the flow output port. The received indication of the sensor signal may be received at the controller directly from the sensor or via an intermediate device or memory, for example. In an embodiment, at the block 302, the method 300 may include receiving indications of multiple sensor signals. For example, the block 302 may include receiving indications of the amount or the flow rate of the fluid that is being delivered from the external fluid source to the user, the amount or the flow rate of ambient air that is being drawn into the interior of the enclosure via the ambient air opening(s) of the enclosure, a sensed level of pressure within the interior of the enclosure, a sensed temperature and/or humidity level within the interior of the enclosure, and/or other sensed conditions associated with the operations of the PRIS.

At a block 305, the method 300 includes determining, by the controller and based on the indication of the sensor signal(s), one or more adjustments to the one or more control elements associated with the PRIS. For example, the controller may execute a control loop or control routine (which, in an implementation, may comprise a set of computer-executable instructions that are stored on one or more memories of the controller and that are executable by one or more processors of the controller) to determine the one or more adjustments. The sensor signal may be an input process variable to the control loop, the desired pressure level that is to be maintained within the interior of the enclosure may be a setpoint utilized by the control loop, and the control loop may subsequently generate indications of the one or more adjustments as an output, for example, as one or more control signals. Of course, in other implementations, the adjustments may be determined by some other type of function and/or logic sequence, and/or indications of the one or more adjustments may include other types of signals or messages.

At a block 308, the method 300 includes transmitting, by the controller via the one or more communication interfaces, indications of the one or more adjustments to the one or more control elements, thereby causing the one or more control elements to control, in accordance with the one or more adjustments, an amount and/or a rate of an inflow and/or an outflow associated with the PRIS, and thereby maintaining a desired level of negative pressure within the interior of the enclosure. The one or more control elements may control, for example, the amount or the flow rate of the interior air that is being drawn through the flow output port, the amount or the flow rate of the fluid that is being delivered from the external fluid source to the user, and/or the amount or the flow rate of ambient air that is being drawn into the interior of the enclosure via the ambient air opening(s) of the enclosure. For example, the one or more control elements may correspond to control valves that are respectively coupled to the external fluid source, the tubing that delivers fluid from the external fluid source into the interior of the PRIS's enclosure, the positive airway pressure device worn by the user, the negative pressure source, the hose or tube interconnecting the negative pressure source with the flow output port of the PRIS's enclosure, the flow output port, an ambient air port, and/or other components that are included and/or associated with the PRIS. The indications of the one or more adjustments may be the one or more control signals generated by the control loop of block 305, or may be other types of indications.

In some embodiments, a user instruction or command initiates an execution of the method 300. In some embodiments, the controller automatically initiates an execution of the method 300, e.g., upon expiration of a timer, upon an occurrence of a triggering event such as an alarm or an alert, a changed sensor value, etc., and/or repeatedly over some interval of time.

In some embodiments, the controller includes or is communicatively connected to, e.g., via the one or more communication interfaces, a user interface via which commands and/or instructions may be received from an operator. For example, an operator of the PRIS may enter instructions via a user interface of a portable computing device, a website, or a portal. Operator instructions may include, for example, an instruction to modify the desired level of negative pressure; an instruction to at least one of add, delete, or modify one or more alarm settings or alert settings associated with the PRIS; an instruction to modify the control loop and therefore how the one or more adjustments are determined at the block 305; an instruction to transmit, via the one or more communication interfaces to at least one of one or more user interfaces and/or other computing devices, data corresponding to operations of the PRIS associated with the user; and/or other instructions related to controlling the pressure within the interior of the enclosure of the PRIS. For example, data corresponding to operations of the PRIS associated with the user may be transmitted to another computing device that administers electronic medical records.

The user interface via which the instructions are received from the operator and/or the recipient user interfaces and/or computing devices may be communicatively connected with the controller via one or more wired and/or wireless links, for example. In some implementations, the user interface via which the instructions are received from the operator and/or the recipient user interfaces and/or computing devices may be communicatively connected via one or more networks.

Figure 4:
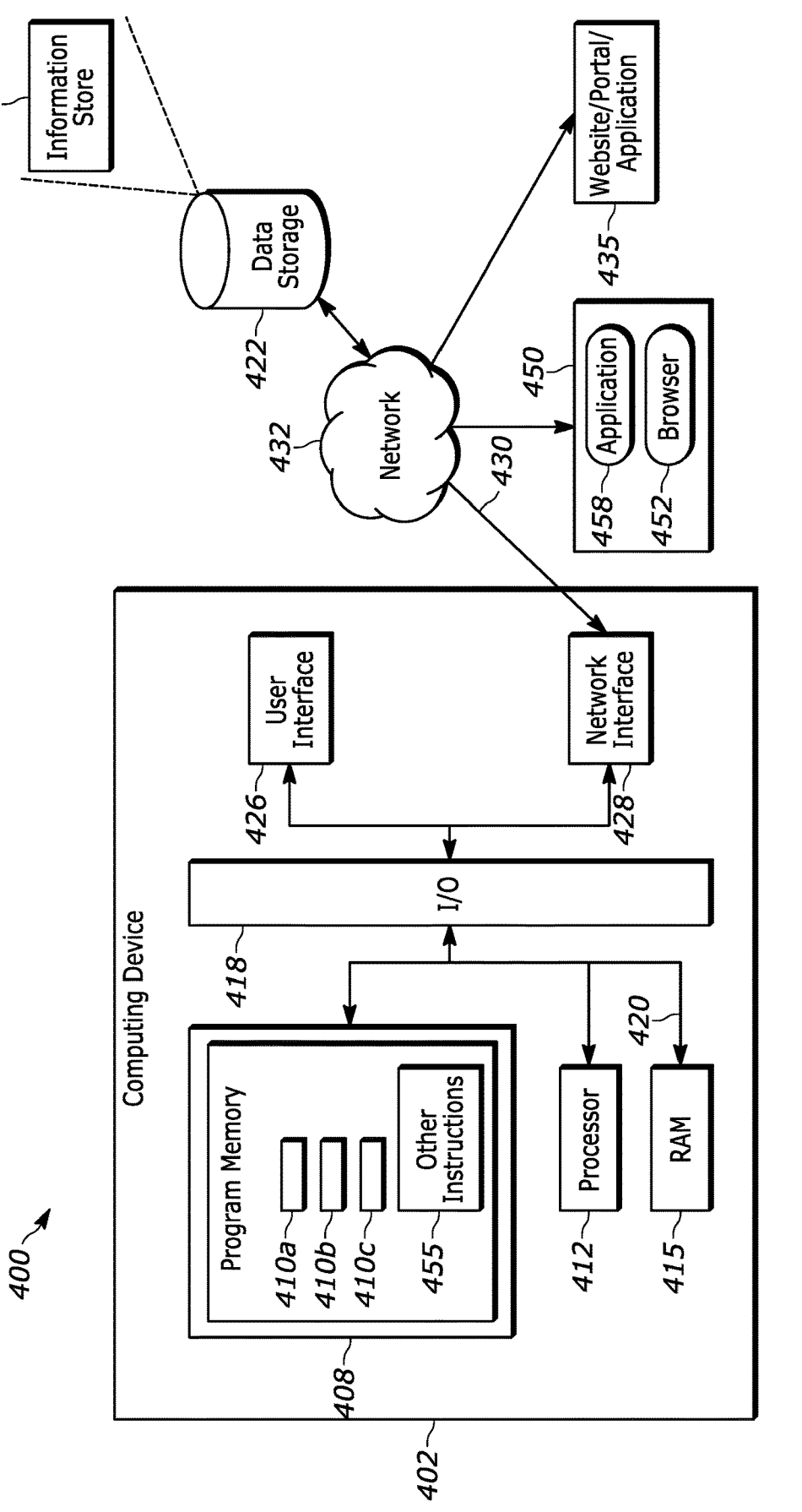
FIG. 4 is a block diagram of an example computing system which may be used in conjunction with embodiments of the PRIS.

FIG. 4 is a block diagram of an example computing system 400 which may be used in conjunction with embodiments of the PRIS, such as the embodiment 100, the embodiment 200, and/or other embodiments. The system 400 includes one or more computing devices 402 that are particularly configured to automatically control one or more components of the PRIS, e.g., control flow control valves and/or sensors associated with the ambient air input port, the flow inlet, the tubing, and/or the flow output port. As such, the computing device 402 may be communicatively connected (e.g., via one or more wired and/or wireless network interfaces 428) to one or more components of the PRIS that are subject to automatic control, such as the one or more control elements described above with respect to the method 300. The system 400 may include a user interface 426 via an operator of the PRIS may set thresholds, modify and/or configure control loops or control routines, set desired alarms or alerts, set desired pressure levels, etc. Thresholds, configurations, alarm/alert levels, desired pressure levels, flow control instructions, and/or obtained flow data may be stored in a data or information store 405. Further, in some embodiments, the embodiment of the computing device 402 shown in FIG. 4 may perform at least portions of one or more methods to control one or more components of and/or associated with the PRIS. For example, instances of the computing device 402 may include the controller, a computing device that includes the user interface via which operator instructions are received, and/or recipient computing devices such as described above with respect to the method 300 of FIG. 3.

As illustrated in FIG. 4, the one or more computing devices 402 associated with the PRIS may include, for example, a computer, a portable computing device (such as a tablet, a laptop, a mobile device, etc.), a server, a plurality of networked or banked computing devices or servers having a logical appearance of a single computing device or server, a plurality of cloud computing devices, etc. Accordingly, for ease of discussion only and not for limitation purposes, the set of computing devices 402 is referred to herein using the singular tense, although in some embodiments the computing device 402 may include more than one physical computing device.

The computing device 402 may include a program memory 408 storing one or more sets of computer-readable and/or computer-executable instructions, e.g., instructions 410a-410c, a processor 412 (e.g., a controller, a microcontroller, a microprocessor, etc.), a random-access memory (RAM) 415, and an input/output (I/O) circuit 418, all of which may be interconnected via an address/data bus 420. The program memory 408 may comprise one or more tangible, non-transitory computer-readable storage media and/or devices, and the computer-readable and/or computer-executable instructions 410a-410c stored thereon, when executed by the processor 412, may cause the computing device 402 to perform control of one or more components of the PRIS.

In doing so, the computing device 402 may access one or more data or memory storage devices 422 at which data corresponding to the system 400 and to the PRIS may be stored. The one or more data storage devices 422 may comprise, for example, one or more memory devices, a data bank, cloud data storage, and/or one or more other suitable data storage devices. Indeed, the one or more data storage devices 422 may include one physical device, or the one or more data or memory storage devices 422 may include more than one physical device. The one or more data storage devices 422, though, may logically appear as a single data storage device irrespective of the number of physical devices included therein. Accordingly, for ease of discussion only and not for limitation purposes, the data storage device 422 is referred to herein using the singular tense.

In one embodiment (not shown), at least one of the one or more data storage devices 422 may be included in the computing device 402, and the processor 412 of the computing device 402 (or the instructions 410 executed by the processor 412) may access the one or more data storage devices 422 via a link comprising a read or write command, function, application programming interface, plug-in, operation, instruction, and/or similar (which may, in turn, also be provided by the computing device 402, an embodiment).

In the present embodiment illustrated in FIG. 4, though, the computing device 402 is shown as being configured to access the one or more data storage devices 422 via one or more network or communication interfaces 428 that are respectively coupled to a link 430 in communicative connection with the one or more data storage devices 422. The link 430 in FIG. 4 is depicted as a link to one or more private and/or public networks 432 (e.g., the one or more data storage devices 422 may be remotely located from the computing device 402), however, the network 432 is not required for the computing device 402 and the data storage device 422 to be communicatively connected. For example, the link 430 may provide a direct connection between the computing device 402 and the data storage device 422. The link 430 may include one or more wired links and/or one or more wireless links, and/or may utilize any suitable communications technology. The network 432 may include one or more proprietary networks, the public Internet, one or more virtual private networks, and/or some other type of network, such as dedicated access lines, plain ordinary telephone lines, satellite links, data networks, combinations of these, etc.

Additionally or alternatively, the system 400 may include and the network 432 may communicatively connect one or more computing devices that host one or more websites, portals, server applications, remote applications, customer-facing processes, etc. (reference 435). For example, the website/portal computing device 435 may host a website, portal, or other remote application via which a user may enter thresholds, control routine modifications, alarm or alert settings, and the like, e.g., via the computing device 402.

As depicted in FIG. 4, a separate computing device 450 being operated by an operator may be communicatively connected to the computing device 402. The computing device 450 may be, for example, a stationary or portable computing device (such as a tablet, a laptop, a mobile device, etc.). In an example, the operator's computing device 450 may be communicatively connected with the computing device 402 via a browser 452 executing on the user's computing device 450 and a website and/or portal. In some embodiments, a user's computing device 450 may communicatively connect to the computing device 402 by using an application 458 (e.g., a local software and/or client application) stored and/or executing thereon. For example, a user may download a client application 458, e.g., from the computing device 402, the host device of the external website and/or application 435, and/or the data storage device 422. Subsequently, the client application 458 and the instructions 408 may establish a secure connection (e.g., a secured session) for communications therebetween over the network 432, e.g., via the computing device 402. The browser 452 or the application 448 may provide a user interface that is communicatively connected to the computing device 402. In this manner, the computing device 402 may act as a server to support multiple operators respectively operating multiple computing devices 450 to control different PRISs, e.g., that are disposed in different locations.

It is noted that while in FIG. 4, the computing device 402, the data storage device 422, and the other computing devices 435, 450 included in the system 400 are illustrated as separate and distinct entities, this is only one of many embodiments. Any number of any of the devices 402, 422, 435, 450 may be included in the network 432, for example. Additionally or alternatively, any number of any of the devices 402, 422, 435, 450 may be a logical, combined or integral device or set of devices. For example, the computing device 402 may host the website(s) and/or portal(s) 435.

With particular regard to the computing device 402, in addition to the instructions 410, the program memory 408 may store thereon further computer-readable or computer-executable instructions 455 that further particularly configure the computing device 402 and that may be executed in conjunction with PRIS control applications. For example, the other instructions 455 may execute to allow a user to produce reports, integrate PRIS information with a patient's electronic medical records, and the like.

In some embodiments, at least a portion of the other instructions 455 may be integral with at least a portion of the instructions 410.

Further, with regard to the computing device 402, while the instructions 410 are shown as three different blocks 410a, 410b, 410c in FIG. 4, it will be appreciated that the instructions 410 may include any number of different programs, modules, routines, and/or sub-routines that may collectively cause the computing device 402 to implement their respective functionality. Similarly, while the other instructions 455 is shown as a single block, it will be appreciated that the other instructions 455 may include a number of different programs, modules, routines, and/or sub-routines that may collectively cause the computing device 402 to implement the other instructions 455.

Still further, it should be appreciated that although only one processor 412 is shown, the computing device 402 may include multiple processors 412. Additionally, although the I/O circuit 418 is shown as a single block, it should be appreciated that the I/O circuit 418 may include a number of different types of I/O circuits. Similarly, the memory of the computing device 402 may include multiple RAMs 415 and/or multiple program memories 408. Further, while the instructions 410, and/or the other instructions 455 are shown being stored in the program memory 408, any or all of the instructions 410, 455 may additionally or alternatively be partially or entirely stored in the RAM 415 and/or other suitable local memory (not shown).

The RAM(s) 415 and/or program memories 408 may be implemented as semiconductor memories, magnetically readable memories, chemically or biologically readable memories, and/or optically readable memories, and/or may utilize any suitable memory technology or technologies. The computing device 402 may also be operatively connected to the network 432 via the link 430 and the I/O circuit 418, in some embodiments.

Thus, in view of the above, the Personal Respiratory Isolation System (PRIS) provides multiple, significant benefits and advantages. Significantly, the PRIS provides a personalized, negative pressure environment for a wearer that has been diagnosed with or is suspected of having a transmissible respiratory illness, such as (but not limited to) COVID-19, thereby reducing contamination of the environment in which the wearer or use is located, as well as reducing the potential spread of viral and/or bacterial pathogens which may be present in the user's fluid outflow. Advantageously, the PRIS is compatible with and functions in conjunction with direct, positive airway pressure devices utilized by the wearer or user, even when such devices cause the user to more often exhale or expel outflow fluid (e.g., aerosolization), such as when the devices operate in a heated manner (e.g., high flow nasal cannulas) and/or when such devices are not well tolerated by the user. Additionally, due to at least the ambient air drawn into the interior of the PRIS's enclosure, the interior of the enclosure is cooled for the user's comfort. Further, the PRIS allows for user mobility as the PRIS may travel with the user to procedures, advanced imaging labs, the restroom, and the like. Still further, embodiments of the PRIS which include lift-able shields allow the user to eat and drink while simultaneously reducing the risks of contaminating surrounding environments.

Moreover, use of the PRIS within medical settings such as hospitals may alleviate the number of patients who need to be held in negative pressure rooms and/or emergency rooms. For example, patients who have or are suspected of having transmissible respiratory illnesses may don respective PRISs within waiting rooms or other areas in which the general population is located instead of taking up valuable beds within negative pressure rooms and/or emergency rooms, even when such patients are not wearing and/or are not in need of therapeutic respiratory devices such as HFNCs, oxygen masks, etc. Further, in embodiments of the PRIS in which therapeutic treatments are delivered to wearer (e.g., via the patient wearing a therapeutic respiratory device while utilizing the PRIS), the use of such PRISs is particularly advantageous for patients who need respiratory treatment, but are able to receive therapeutic benefits without the use of a mechanical ventilator, thereby freeing up mechanical ventilators for other patients with more serious respiratory conditions, as well as minimizing needless and/or premature use of more invasive procedures (e.g., intubation). Accordingly, use of the PRIS not only reduces the risk of contamination and pathogen spread, but also alleviates the shortages of limited, critical medical resources such as Personal Protective Equipment that is utilized by health care workers, space in negative pressure rooms, and mechanical ventilators, to name a few, and further, allows a certain population of patients to be less invasively treated.

Figure 5:
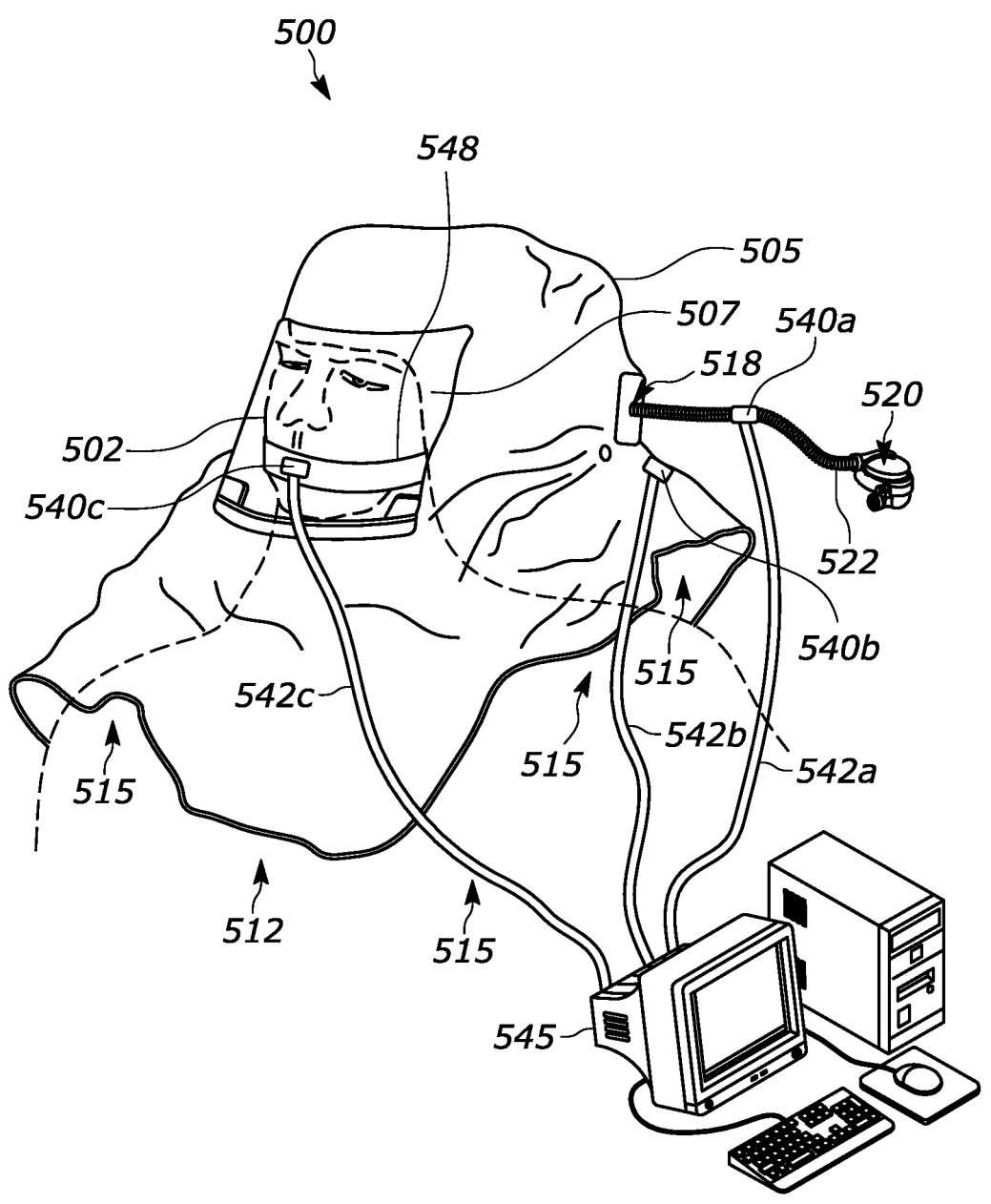
FIG. 5 is a block diagram of an embodiment of a PRIS that detects and/or monitors a fluid outflow of a user.

FIG. 5 is a block diagram of an example Personal Respiratory Isolation System 500 configured to detect and/or monitor one or more characteristics of a fluid outflow of a user. The PRIS 500 may be an embodiment of the PRIS 100, an embodiment of the PRIS 200, or another embodiment of a PRIS. The PRIS 500 may operate in conjunction with the method 300 and/or with other methods associated with PRIS usage, for example. The PRIS 500 may include one or more instances of at least portions of the example computing system 400, in embodiments.

In FIG. 5, the PRIS 500 is shown as being utilized by a user 502. The PRIS 500 includes an enclosure 505 which may comprise one or more rigid portions and/or one or more flexible portions, and the interior of the enclosure 505 is denoted in FIG. 5 by the reference 507. The enclosure 505 includes an aperture 512 via which the head, neck, and at least part of the shoulders of the user 502 have been received into the interior 507 of the enclosure 505, although in other embodiments, alternate, less, or more body parts of the user 502 may have been received into the interior 507 of the PRIS's enclosure 505. The PRIS 500 includes a flow output port 518 to which a negative pressure source 520 is coupled, e.g., via a hose or a tube 522. The negative pressure source 520 is operable to draw ambient air into the enclosure's interior 507 via one or more openings 515 of the enclosure 505, and to draw air disposed within the interior 507 through the flow output port 518 to thereby create a personal, negative pressure environment surrounding the user 102 within the interior 507 of the PRIS 500, e.g., in a manner similar to that described above.

As depicted in FIG. 5, the PRIS 500 includes one or more outflow sensors 540a, 540b, 540c, each of which is communicatively connected via respective links 542a, 542b, 542c to an outflow user interface 545. Generally speaking, the links 542 may include any number of wired links and or wireless links. In some implementations, some of the links 542a-542c may be shared by multiple outflow sensors 540a-540b, such as when some of the links 542a-542c are implemented using a wireless network.

The one or more outflow sensors 540a-540c are respectively positioned and configured to detect one or more characteristics of a fluid outflow generated by the user 502. The user's fluid outflow may include fluid outflow that is exhaled by the user 502, and optionally may include fluid outflow that is otherwise expelled by the user 502. For example, as illustrated in FIG. 5, outflow sensor 540a is positioned external to the enclosure 505 to detect one or more characteristics of the fluid outflow that is drawn from the interior 507 of the enclosure 505 through the flow output port 518. Outflow sensor 540b is positioned within the interior 507 of the enclosure 505 to detect one or more characteristics of the air disposed within the interior 507 of the enclosure 505, which may include the fluid outflow of the user 502. Outflow sensor 540c is positioned on, integral with, included in or otherwise used in conjunction with a device 548 that is worn by the user 502 within the interior 507 of the enclosure 505 (such as a face mask, cannula, etc.) to more directly detect (as compared with sensor 540a, 540b) one or more characteristics of the fluid outflow generated by the user 502. At least some of the outflow sensors 540a-540c may be positioned in a pre-filtering or a post-filtering position (e.g., with respect to the one or more filters described herein) using respective adaptors, if desired. Further, although the PRIS 500 is illustrated in FIG. 5 with three outflow sensors 540a-540c, any number of one or more outflow sensors may be utilized in conjunction with the PRIS 500.

The one or more characteristics detected by the user outflow sensors 542a-542c may include, for example, a volume of user fluid outflow, a rate of user fluid outflow, and/or respective levels of various components included in the user fluid outflow, such as oxygen levels, levels of various aerosolized therapeutics and/or medicines that have been used to treat the user 502, pathogens (such as viruses and/or bacteria), volatile organic compounds, volatile inorganic compounds, and/or other characteristics.

The outflow user interface 545 may include a visual display, auditory signals (such as auditory steady state indicators, alerts, alarms, etc.), and/or any other type of desired user interface. Generally, the outflow user interface 545 may present thereon respective indications of the one or more characteristics detected by the one or more outflow sensors 540a-540c, such as numerical values, graphical representations, statuses, alerts, alarms, and the like. In some embodiments, the outflow user interface 545 may be included in a monitoring device that continuously monitors the one or more characteristics of the user fluid outflow over time, e.g., based on periodic and/or updated signals generated by the user outflow sensors 540a-540c.

In some embodiments, the outflow user interface 545 may be included in and/or communicatively connected to one or more computing devices (not shown in FIG. 5). At least some of the one or more computing devices may be locally disposed (e.g., proximate to the user 502), and/or at least some of the one or more computing devices may be remotely disposed, e.g., in a manner such as described with respect to FIG. 4. The one or more computing devices may store the information indicative of the one or more characteristics detected by the one or more user outflow sensors 540a-540c. For example, the one or more computing devices may administer medical records, and as such may store the information indicative of the one or more characteristics detected by the one or more user outflow sensors 540a-540c in conjunction with one or more electronic medical records corresponding to the user 502. Additionally or alternatively, the one or more computing devices may perform analytics using the information indicative of the one or more characteristics detected by the one or more user outflow sensors 540a-540c. For example, the one or more computing devices may execute one or more analytics modules, programs, and/or routines that operate on the information indicative of the one or more characteristics detected by the one or more user outflow sensors 540a-540c, and optionally may operate on other information corresponding to the user 502 and/or to other users and/or patients.

Advantageously, the information indicative of the one or more characteristics detected by the one or more user outflow sensors 540a-540c that is presented on the outflow user interface 545 may be utilized to determine a diagnosis of a medical condition of the user 502 and/or to determine a treatment plan for the user 502. For example, local medical personnel may observe changing values of user outflow characteristics on an outflow user interface 545 of a locally disposed monitoring device, and may take mitigating and/or emergency actions when necessary. In another example, information indicative of the user's outflow characteristics may be aggregated with that of other users, and may be analyzed to discover new information at a population level, such as characteristics of disease progression, treatment efficacies, and the like.

ADDITIONAL CONSIDERATIONS

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed is:

1. A personal respiratory isolation system (PRIS), comprising:

an enclosure configured to be worn by a user while the user is mobile, the enclosure having:

an aperture configured to receive only a portion of a body of the user into an interior of the enclosure so that a nose and a mouth of the user are contained within the enclosure, the interior of the enclosure being unsealed from an environment in which the user is located via one or more gaps provided by unsealed components of the enclosure, and the one or more gaps including the aperture;

one or more rigid portions, at least a part of which is disposed to shield the nose and the mouth of the user from the environment in which the user is located while the nose and the mouth of the user are contained within the enclosure, the at least the part of the one or more rigid portions which is disposed to shield the nose and the mouth of the user being a shield; and a flow output port coupled to a negative pressure source, the negative pressure source disposed outside of the enclosure and operable to draw ambient air from the environment via the one or more gaps into the interior of the enclosure and simultaneously draw at least one of air or fluid that is disposed within the interior of the enclosure through the flow output port to thereby provide a negative pressure within the interior of the enclosure and cause the air and/or fluid that is drawn through the flow output port to be at least one of filtered to collect pathogenic particles or treated by a pathogen-impairing technique, the air and/or fluid that is drawn through the flow output port including fluid that has been at least one of exhaled or expelled by the user.

2. The personal respiratory isolation system of claim 1, further comprising the negative pressure source.

3. The personal respiratory isolation system of claim 1, wherein the shield is sized to shield an entirety of a face of the user.

4. The personal respiratory isolation system of claim 1, wherein the shield is at least partially removable from the enclosure via one or more attachment mechanisms.

5. The personal respiratory isolation system of claim 1, wherein the shield is a first portion of the one or more rigid portions, and a second portion of the one or more rigid portions of the enclosure is disposed to cover a non-facial portion of a head of the user while the nose and the mouth of the user are contained within the enclosure.

6. The personal respiratory isolation system of claim 1, wherein the ambient air is drawn from the environment into the interior of the enclosure via the aperture, the aperture is at least partially formed by the one or more rigid portions, and the user enters into the enclosure via the aperture.

7. The personal respiratory isolation system of claim 1, wherein the portion of the body of the user received into the aperture excludes shoulders of the user, and the PRIS further comprises one or more flexible portions disposed to cover at least one of: at least a portion of a neck of the user or a non-facial portion of a head of the user while the nose and the mouth of the user are contained within the enclosure.

8. The personal respiratory isolation system of claim 7, wherein the ambient air is drawn into the interior of the enclosure from the environment via one or more cracks or gaps that are inherently provided by the one or more flexible portions.

9. The personal respiratory isolation system of claim 1, wherein the fluid that has been at least one of exhaled or expelled by the user is a first fluid, and the PRIS further comprises a flow inlet configured to receive tubing via which a second fluid is delivered from an external fluid source into the interior of the enclosure for at least one of inhalation or ingestion by the user.

10. The personal respiratory isolation system of claim 9, wherein the aperture includes the flow inlet.

11. The personal respiratory isolation system of claim 9, wherein:

the second fluid includes at least one of oxygen, a medication, or a therapeutic;

the tubing is coupled to a device that is disposed within the interior of the enclosure and via which the second fluid is delivered to the user; and the device is one of a nasal cannula, a face mask, a Continuous Positive Airway Pressure (CPAP) device, a multi-level Positive Airway Pressure device, or another type of cannula or respiratory device.

12. The personal respiratory isolation system of claim 1, wherein at least one of:

the flow output port or the negative pressure source includes one or more respective filters through which the ambient air and the at least one air or fluid that is disposed within the interior of the enclosure are simultaneously drawn prior to being vented into the environment, the one or more respective filters include at least one of: a high-efficiency particular air (HEPA) filter, a passive carbon filter, an active carbon filter, a medical grade air filter, or another type of air filter; or the ambient air and the at least one of the air or fluid that is disposed within the interior of the enclosure are simultaneously drawn through the flow output port are exposed to the pathogen-impairing technique prior to being vented into the environment, the pathogen-impairing technique utilizing at least one of: ultra-violet radiation, a high temperature chamber, or another process or device that impairs at least one of a bacteria or a virus.

13. The personal respiratory isolation system of claim 1, further comprising a controller communicatively connected to one or more control elements associated with the PRIS, the controller configured to:

receive, via one or more communication interfaces, an indication of a signal generated by a sensor, the signal indicative of an amount or a flow rate of the air and/or fluid that is drawn through the flow output port;

determine, based on the indication of the signal, one or more adjustments to the one or more control elements; and transmit, via the one or more communication interfaces, indications of the one or more adjustments to the one or more control elements, thereby causing the one or more control elements to control, in accordance with the one or more adjustments, the amount or the flow rate of the air and/or fluid that is drawn through the flow output port, thereby maintaining a desired level of negative pressure within the interior of the enclosure.

14. The personal respiratory isolation system of claim 13, wherein:

the fluid that has been at least one of exhaled or expelled by the user is a first fluid, the sensor is a first sensor, and the signal is a first signal;

the enclosure of the PRIS further includes a flow inlet via which tubing is received into the interior of the enclosure, the tubing fluidly connected to an external fluid source and delivering a second fluid for at least one of inhalation or ingestion by the user; and the controller is further configured to:

receive, via the one or more communication interfaces, an indication of a second signal generated by a second sensor, the second signal indicative of an amount or a flow rate of the second fluid that is being delivered, via the tubing, to the user;

determine the one or more adjustments to the one or more control elements is further based on the indication of the second signal; and transmit the respective indications of the one or more adjustments thereby causing the one or more control elements to control, in accordance with the one or more adjustments, at least one of: (i) the at least one of the amount or the flow rate of the air and/or fluid that is drawn through the flow output port, or (ii) the amount or the flow rate of the second fluid that is being delivered to the user.

15. The personal respiratory isolation system of claim 14, wherein the one or more control elements control the at least one of: (i) the at least one of the amount or the flow rate of the air and/or fluid that is drawn through the flow output port, or (ii) the amount or the flow rate of the second fluid that is being delivered to the user by sending respective control signals to at least one of: the external fluid source, the negative pressure source, an input flow control valve coupled to the tubing, or an output flow control valve coupled to the flow output port.

16. The personal respiratory isolation system of claim 13, wherein the sensor generates updated signals over an interval of time, and the receive, determine, and transmit steps are repeatedly executed by the controller over the interval of time in accordance with the updated signals generated by the sensor.

17. The personal respiratory isolation system of claim 13, wherein the receive, determine, and transmit steps are automatically initiated and executed by the controller.

18. The personal respiratory isolation system of claim 13, wherein the controller is further configured to receive, via the one or more communication interfaces, an indication of one or more user instructions, the one or more user instructions including at least one of:

an instruction to modify the desired level of negative pressure;

an instruction to at least one of add, delete, or modify one or more alarm settings or alert settings associated with the PRIS;

an instruction to modify the determining of the one or more adjustments; or an instruction to transmit, via the one or more communication interfaces to at least one of a user interface or another computing device, data corresponding to operations of the PRIS associated with the user.

19. The personal respiratory system of claim 1, further comprising:

one or more user outflow sensors positioned to detect one or more characteristics of a fluid outflow of the user, the user fluid outflow including the fluid that has been at least one of exhaled or expelled by the user, and the one or more characteristics including at least one of a volume of the user fluid outflow, a rate of the user fluid outflow, or respective levels of one or more components of the user fluid outflow; and an outflow user interface that is communicatively connected to the one or more user outflow sensors and via which information indicative of the one or more characteristics of the user fluid outflow is presented.

20. The personal respiratory system of claim 19, wherein the one or more user outflow sensors and the outflow user interface are included in a monitoring device that continuously monitors the one or more characteristics of the user fluid outflow and updates the information indicative of the one or more characteristics accordingly.

* * * * *